United States Patent [19]

Babayan

[11] 4,205,086

[45] May 27, 1980

[54] METHOD FOR THE TREATMENT OF GALLSTONES

[75] Inventor: Vigen K. Babayan, Indianapolis, Ind.

[73] Assignee: Stokeley-Van Camp, Inc., Indianapolis, Ind.

[21] Appl. No.: 857,001

[22] Filed: Dec. 2, 1977

[51] Int. Cl.$^2$ .................... A61K 31/23; A61K 31/20; A61K 31/22; A61K 31/19

[52] U.S. Cl. .................................. 424/312; 424/311; 424/317; 424/318

[58] Field of Search ................ 424/312, 318, 317, 311

[56] References Cited

FOREIGN PATENT DOCUMENTS 2209044  8/1973  Fed. Rep. of Germany ........... 424/312

OTHER PUBLICATIONS

Greenberger et al.,—*New England Journal of Medicine*, 280, 1045–1058 May 8, 1969.
*Biological Chemistry*, 1966, pp. 513–520, Mahler et al., Dept. of Chem., Indiana Univ.-Harper & Row, Pub., NY & London.
*Principles of Biochem.* 2nd Ed., (1959) Mcgraw-Hill Book Co. Inc., New York, Toronto, London, pp. 459–465.
Kritchevsky et al., "Solubility of Cholestrol in Various Fats and Oils".

*Primary Examiner*—Frederick E. Waddell
*Attorney, Agent, or Firm*—Woodard, Weikart, Emhardt & Naughton

[57] ABSTRACT

A method for the treatment of gallstones is disclosed herein which comprises perfusing adjacent the gallstones a liquid form of a physiologically-compatible mixture of fatty acids and/or alcohol esters of fatty acids. The mixture preferably comprises octanoic acid and decanoic acid, and the gylcerol esters thereof.

21 Claims, No Drawings

METHOD FOR THE TREATMENT OF GALLSTONES

BACKGROUND OF THE INVENTION

1. Field of the Invention

The present invention relates to a method for the treatment of gallstones, and more particularly to a method involving the perfusion of a solvent adjacent the gallstones.

2. Description of the Prior Art

Gallstones occur in a significant number of persons, with obesity and pregnancy being among the known predisposing factors. The causes of the formation of gallstones, more particularly known as biliary calculi, are generally obscure, with biliary stasis and disrupted cholesterol metabolism having been suggested as possible causative factors. Gallstones generally are found in the gallbladder, a condition known as cholelithiasis, or in the common duct, a condition known as choledocholithiasis. Gallstones are generally of three types, pure pigment stones of calcium bilirubinate which occur in hemolytic diseases, cholesterol stones, and mixed stones, the latter two types accounting for 80% of stone occurences.

Patients having gallstones may be completely asymptomatic for long periods. However, gallstones are generally accompanied by biliary colic, frequently with jaundice. Nausea and vomiting may also exist, and frequently the patient experiences regional pain and tenderness, as well as upper abdominal discomfort.

The treatment for gallstones in the past has followed two general courses. Immediate relief of the pain and discomfort associated with gallstones is generally attempted through the use of antispasmodics, such as amyl nitrite, nitroglycerin or atropine. Analgesics, such as meperidine, which also has some antispasmodic action, or stronger medicines in the case of more severe pain, may also be necessary. Typically, a low-fat high-protein, high-carbohydrate diet is recommended to lessen the likelihood of repeated attacks and to reduce the operative risk in subsequent surgery.

The potential for developing acute cholecystitis and its complications has generally meant in the past that surgery, known as cholecystectomy (removal of the gallbladder), would be required. Mortality associated with this operative technique is low, although the mortality rate is high due to resultant complications, particularly in poor-risk patients. Alternatively, surgical procedures may include mechanical stone extraction through the T-tube tract or retrograde endoscopic sphincterotomy, but these approaches may be contraindicated or unsuccessful.

A number of solvents have been proposed in the prior art for the dissolution of gallstones by the process of infusion or perfusion. Organic solvents such as ether, chloroform and d-limonene have been used, but these solvents are poorly tolerated by patients and are potentially toxic, without highly favorable results. Oxycholic acid and sodium cholate in 100-200 mM solutions have shown definite but low solubilizing capacities for gallstones. Uncontrolled studies with these compounds have reported disappearance of distal common bile duct stones in 1-4 weeks, but often with bile acid diarrhea. Kenodeoxycholic acid has been found to be more preferable, but also is relatively slow and may result in problems with repeated use. The use of heparin in saline solution has also been found to function poorly to fragment or dissolve gallstones.

Prior art studies directed at controlling the level of cholesterol in blood serum have noted the solubility of cholesterol in the short chain fatty acids and their esters. A number of patents have issued relating to compositions or methods directed toward reducing the cholesterol level in blood serum by administration of acid or ester compounds, as exemplified by U.S. Pat. No. 3,495,011, issued to Fossel on Feb. 10, 1970, and U.S. Pat. No. 3,158,541, issued to Sutherland on Nov. 24, 1964. Each of the prior art disclosures of this type, however, are concerned with compounds, typically administered orally, for the general reduction of the cholesterol level in the blood.

In an article entitled "Solubility of Cholesterol in Various Fats and Oils", authored by David Kritchevsky and Shirley A. Tepper of the Wistar Institute of Anatomy and Biology, Philadelphia, Pennsylvania, the results of solubility tests for cholesterol in medium chain triglycerides are recited. This article was concerned with the effect of fatty acid diets on serum cholesterol levels, and concluded that solubility measurements in vitro do not correlate with the effects of the various fats on serum cholesterol levels.

SUMMARY OF THE INVENTION

The present invention provides a method for the treatment of cholesterol-containing gallstones which comprises perfusing adjacent the gallstones a liquid form of fatty acids and/or alcohol esters thereof. The acids and esters utilized in the present invention are physiologically-compatible and preferably have short to medium carbon chain lengths.

It is an object of the present invention to provide a method for the treatment of gallstones which is highly effective, and yet simply and readily performed.

Another object of the present invention is to provide a method for the treatment of gallstones which utilizes a solvent for dissolution of the gallstones, which solvent does not produce adverse effects for the patient.

It is a further object of the present invention to provide a method for the treatment of gallstones which is very safe and in many instances obviates the need for cholecystectomy and similar surgical techniques.

It is another object of the present invention, in a particular embodiment thereof, to provide a method for the treatment of gallstones which utilizes solvents that are the natural hydrolysis products of triglycerides in metabolic processes, and which are therefore safe in use.

Futher objects and advantages of the present invention will become apparent from the Description of the Preferred Embodiments which follows.

DESCRIPTION OF THE PREFERRED EMBODIMENTS

Gallstone treatments in the past have generally included surgical removal of the gallstones and/or dietary controls. The use of solvents in an infusion or perfusion technique has been proposed in the prior art, but the solvents which have heretofore been utilized have been found to be inadequate or to have adverse effects on patients. The present invention provides a perfusion technique utilizing a solvent which is both fast and highly efficient, and which also is fully safe and does not produce adverse side effects.

In accordance with the method of the present invention a selected compound is perfused adjacent the gallstone. For the purposes herein, the term perfusion is intended to encompass the introduction of the compound in a manner that will cause the compound to pass over or around the subject gallstone, and includes equivalent terms such as infusion. The perfusion may be accomplished in accordance with normal procedures, and for example may be performed with a T-tube or an endoscope. The compound utilized by the present invention thereby contacts and gradually dissolves the gallstone. The response of the gallstone to this procedure may be followed, for example, by repeated cholangiograms.

The compound utilized by the present invention comprises one or more fatty acids and/or their alcohol esters. It is of course required that the compound be physiologically-compatible in view of the application of the present method. The compound is also required to be in liquid form during the perfusion process, which consequently means that the compound must be liquid at the temperature at which it will be utilized in the present method, or in other words at body temperature. Although it is not necessary, it is preferable that the compound be liquid at room temperature. Certain of the fatty acids and esters which are useful in the present invention are liquid at body temperature but not at room temperature, while others are also liquid at room temperature. It is possible to combine these compounds with others which normally would not be liquid at or below body temperature to provide a liquid form of the latter compounds.

It is also preferable that the compound not be excessively viscous at the perfusion temperature in view of the need for the compound to move through the perfusion equipment and to pass over or around the gallstone. The degree of viscosity which is tolerable, and the compounds therefore useful in the present invention, may be readily determined by experiment. The compounds which are most preferred for use in the present invention are fluid at room temperature and do not display excessive viscosity in the perfusion technique. Fatty acids useful in the present invention are generally those having short to medium carbon chain lengths, or from about 2 to about 12 carbon atoms. Octanoic acid, also known as caprylic acid, has a melting point of 16.3° C. and decanoic acid, also known as capric acid, has a melting point of 31.5° C. Dodecanoic acid, also known as lauric acid and having 12 carbon atoms, has a melting point of 44° C. and the higher fatty acids generally have correspondingly higher melting points. As previously mentioned, these fatty acids which have melting points above body temperature, which is approximately 37° C., may be combined with the fatty acids which are liquid at body temperature to provide a liquid mixture having relatively low proportions of the higher fatty acids.

Also useful in accordance with the method of the present invention are alcohol esters of the fatty acids. It is generally preferred that the esters be of the lower alcohols, including those having multiple hydroxy groups such as the diols and the triols. More particularly, the esters preferably comprise esters of the following alcohols; mono, di and polyhydric alcohols such as methanol, ethanol, propanol, butanol, ethylene glycol (ethanediol), butylene glycol (butanediol), propylene glycol (propanediol) and glycerol (propanetriol).

As is well known in the art, the esters are readily obtainable by one method involving the combination of a fatty acid with an alcohol, with the elimination of a water molecule (esterification). It is to be understood however, that the term "alcohol ester of a fatty acid" is intended to encompass esters not necessarily obtained by this reaction process. Fatty acid esters may be mono-esters, di-esters or a polyester. It has been found that gallstones are particularly soluble in the mono- and di-esters, with the monoglycerides and diglycerides being particularly preferred. As previously indicated, it is required that the esters utilized in the present invention be physiologically-compatible, and be liquid at body temperature when in combination with other acids or esters comprising the compound used in the present invention.

A compound useful in accordance with the method of the present invention may also comprise a mixture of fatty acids and alcohol esters of fatty acids. Typically the fatty acid esters would be esters of the same fatty acids which exist separately in the solution, although such is not required. It is preferred that the fatty acids which exist either as themselves or in the ester form have from about 2 to about 12 carbon atoms, with from about 8 to about 10 carbon atoms being more preferred. In a most preferred embodiment of the present invention, the method comprises the perfusion of a compound having a mixture of fatty acids from about 8 to about 10 carbon atoms and alcohol esters, particularly glycerides, of fatty acids having from about 8 to about 10 carbon atoms. In the latter embodiment, glycerol mono-octanoate, alone or in combination with octanoic acid and/or glycerol mono-decanoate and decanoic acid, has produced excellent results.

The method of the present invention for the treatment of gallstones, particularly with octanoic and decanoic fatty acids and their alcohol esters, has been found to be completely safe and non-toxic and to provide results superior to those obtained with the techniques of the prior art. In practice, gallstones have been found to be completely dissolved within 48 hours in many cases. Compounds such as the mono-glyceride of octanoic acid and propylene glycol mono-octanoate, which have low viscosity and high solvency for the gallstones, have shown particularly excellent results.

EXAMPLE 1

An in vitro study was conducted to compare the solubility of gallstones in glycerol mono-octanoate and sodium cholate. The mono-octanoate solution had a concentration of 11.7 g per 100 ml, and the sodium cholate was a 150 mM solution. Matched stones from 15 patients were obtained, these stones having weights of approximately 0.30 g with the average difference between matched stones being 0.036 g. One of each pair of stones was placed in 20 ml portions of the mono-octanoate solution, with the other stones being similarly placed in 20 ml portions of the sodium cholate solution. The solutions were maintained at 37° C. for 72 hours, with the sodium cholate solution being exchanged daily to minimize the possibility of a micellar saturation effect. The solutions were mixed gently at 24 hour intervals and 2 ml aliquots were removed at such intervals form analysis.

For each pair of stones, the mono-octanoate solution performed superior to the sodium cholate solution in dissolving the stone, and the mono-octanoate averaged dissolving 2.5 times the amount of stone dissolved by the sodium cholate. The ratio of the amount of stone dissolved by the mono-octanoate to the amount of stone dissolved by the sodium cholate ranged from 1.3 to 4.0 after the first day, from 1.7 to 4.6 after the second day and from 1.9 to 4.7 after the third day. The mean ratios for the ratios of amounts dissolved by the respective solutions were 2.2 for the first day, 2.9 for the second day and 3.0 for the third day.

EXAMPLE 2

A test was conducted to compare the solubility of gallstones in glycerol mono-octanoate and in a 200 mM solution of sodium cholate. A solution of the glycerol mono-octanoate as described in Example 1 was utilized. Approximately equal size stones, all being obtained from the same patient, were placed in the two solutions and observed. The stones in the glycerol mono-octanoate progressively decreased in size while the stones in the sodium cholate showed little or no apparent change after six days.

EXAMPLE 3

Studies are conducted to evaluate the solubility of gallstones in a variety of compounds. Gallstones are placed in the various compounds and observed for several days. The compounds utilized include butyric acid, octanoic acid and decanoic acid; ethanol octanoate, butanol decanoate, ethylene glycol mono-octanoate, propylene glycol mono-octanoate, glycerol mono-octanoate, glycerol tri-octanoate and glycerol di-decanoate; and combinations of these fatty acids and fatty esters. The gallstones are found to be suitably soluble in each of these compounds, with high solubility existing for the mono- and di-esters of glycerol.

EXAMPLE 4

The method of the present invention was performed at the Mayo Clinic and Mayo Foundation in Rochester, Minnesota on a ninety-year old patient having at least two large retained distal common bile duct stones, these stones being too large to attempt extraction safely. A glycerol mono-octanoate solution was millipore filtered and perfused at a rate of 5 ml per hour using a constant infusion pump and an in-line central venous pressure manometer. The pressure varied from 5 to 15 cm. After six days only two very small lucencies were apparent, and after 3 additional days there was no evidence of the stones. The patient tolerated the procedure well and showed no adverse symptoms or effects. Similar clinical trials have also been conducted at the Mayo Clinic with equally good results.

EXAMPLE 5

By the fractionation of coconut oil, a mixture was obtained containing about 70% octanoic acid, about 25% decanoic acid and less than 3% each of the higher and lower fatty acids. This mixture was reacted with glycerine in approximately equal molar quantities, with a slight excess of glycerine, to yield the monoglycerides in a conventional manner. The resultant compound displayed the following properties:

| Property | Limit |
| --- | --- |
| Iodine Value | 1.5 max |
| Color, Lovibond Red | 2.5 max |
| Acid Value | 2.5 max |
| Moisture, KF | 0.5% max |
| Monoglycerides, as Oleate | 70% min |
| Free Glycerol | 25% max |
| Specific Gravity (100°) | 0.98-1.01 |
| Appearance | Clear Liquid |
| Viscosity | 40-55 cs |

This material was used clinically in vitro and in vivo in monkeys and humans. The material was found to be highly effective in dissolving gallstones.

While there have been described above the principles of this invention in connection with the specific examples, it is to be clearly understood that this description is made only by way of example and not as a limitation of the scope of the invention.

I claim:

1. A method for gradually dissolving a cholesterol-containing gallstone in a patient which comprises perfusing adjacent the gallstone an effective amount of a liquid form of a physiologically-compatible compound selected from the group consisting of fatty acids, alcohol esters of fatty acids and mixtures of fatty acids and alcohol esters of fatty acids, said perfusion being performed to solubilize at least a portion of the gallstone.

2. The method of claim 1 in which the esters comprise fatty acid esters of compounds selected from the group consisting of mono, di and polyhydric alcohols.

3. The method of claim 2 in which the esters comprise mono, di and polyesters.

4. The method of claim 3 in which the compound comprises esters having from about 8 to about 10 carbon atoms.

5. The method of claim 4 in which the compound comprises glycerides of octanoic acid and decanoic acid.

6. The method of claim 4 in which the compound comprises glycerol mono-octanoate.

7. The method of claim 3 in which the compound comprises a mixture of fatty acids having from about 8 to about 10 carbon atoms and glycerides of fatty acids having from about 8 to about 10 carbon atoms.

8. The method of claim 7 in which the compound comprises a mixture of octanoic acid and glycerol mono-octanoate.

9. The method of claim 7 in which the compound comprises a mixture of octanoic acid, glycerol mono-octanoate, decanoic acid and glycerol mono-decanoate.

10. The method of claim 2 in which the compound comprises a mixture of fatty acids having from about 8 to about 10 carbon atoms and esters of fatty acids having from about 8 to about 10 carbon atoms.

11. The method of claim 1 in which the esters are of fatty acids having from about 8 to about 10 carbon atoms.

12. The method of claim 11 in which the compound comprises propylene glycol mono-octanoate.

13. The method of claim 11 in which the compound comprises ethanol mono-octanoate.

14. The method of claim 1 in which the fatty acids have from about 2 to about 12 carbon atoms.

15. The method of claim 14 in which the fatty acids have from about 8 to about 10 carbon atoms.

16. The method of claim 15 in which the esters are of fatty acids having from about 8 to about 10 carbon atoms.

17. The method of claim 16 in which the compound comprises a mixture of fatty acids and of alcohol esters of fatty acids.

18. The method of claim 17 in which the alcohol esters of fatty acids are glycerides.

19. A method for gradually dissolving a cholesterol-containing gallstone in a patient which comprises perfusing adjacent the gallstone an effective amount of a liquid form of a physiologically-compatible compound selected from the group consisting of glycerol mono-octanoate, octanoic acid, glycerol mono-decanoate, decanoic acid and combinations thereof, said profusion being performed to solubilize at least a portion of the gallstone.

20. A method for gradually dissolving a cholesterol-containing gallstone in a patient which comprises perfusing adjacent the gallstone an effective amount of a liquid form of a physiologically-compatible fatty acid ester of a compound selected from the group consisting of methanol, ethanol, propanol, butanol, ethylene glycol, butylene glycol, propylene glycol, glycerol and combinations thereof, said profusion being performed to solubilize at least a portion of the gallstone.

21. A method for gradually dissolving a cholesterol-containing gallstone in a patient which comprises perfusing adjacent the gallstone an effective amount of a liquid form of a physiologically-compatible compound selected from the group consisting of butyric acid, octanoic acid, decanoic acid, ethanol octanoate, butanol decanoate, ethylene glycol mono-octanoate, propylene glycol mono-octanoate, glycerol mono-octanoate, glycerol tri-octanoate, glycerol di-decanoate and combinations thereof, said profusion being performed to solubilize at least a portion of the gallstone.

* * * * *

UNITED STATES PATENT AND TRADEMARK OFFICE
CERTIFICATE OF CORRECTION

PATENT NO. : 4,205,086
DATED : May 27, 1980
INVENTOR(S) :

It is certified that error appears in the above–identified patent and that said Letters Patent are hereby corrected as shown below:

"Assignee: Stokeley-Van Camp, Inc." should be changed to
--Assignee: Stokely-Van Camp, Inc.--

Signed and Sealed this

Sixteenth Day of September 1980

[SEAL]

Attest:

SIDNEY A. DIAMOND

Attesting Officer     Commissioner of Patents and Trademarks